United States Patent
Murthy et al.

(10) Patent No.: US 9,625,358 B2
(45) Date of Patent: Apr. 18, 2017

(54) GAS SAMPLING APPARATUS AND MONITORING APPARATUS

(75) Inventors: Prakash Sreedhar Murthy, Tsukuba (JP); Akira Imai, Tsukuba (JP)

(73) Assignee: ATONARP INC., Minato-Ku, Tokyo (JP)

( * ) Notice: Subject to any disclaimer, the term of this patent is extended or adjusted under 35 U.S.C. 154(b) by 509 days.

(21) Appl. No.: 14/342,954

(22) PCT Filed: Sep. 4, 2012

(86) PCT No.: PCT/JP2012/005596
§ 371 (c)(1),
(2), (4) Date: Jun. 11, 2014

(87) PCT Pub. No.: WO2013/035306
PCT Pub. Date: Mar. 14, 2013

(65) Prior Publication Data
US 2014/0290340 A1    Oct. 2, 2014

(30) Foreign Application Priority Data

Sep. 6, 2011   (JP) ................................ 2011-194315

(51) Int. Cl.
*G01N 1/02*   (2006.01)
*G01N 1/22*   (2006.01)
(Continued)

(52) U.S. Cl.
CPC ......... *G01N 1/2202* (2013.01); *G01N 1/2226* (2013.01); *G01N 15/06* (2013.01);
(Continued)

(58) Field of Classification Search
None
See application file for complete search history.

(56) References Cited

U.S. PATENT DOCUMENTS 4,477,986 A * 10/1984 Marshall et al. .............. 73/40.7
4,577,490 A *  3/1986 Bray et al. .................... 73/40.7
(Continued)

FOREIGN PATENT DOCUMENTS

EP   0 169 057 A2   1/1986
JP   1-189559 A     7/1989
(Continued)

OTHER PUBLICATIONS

International Search Report (PCT/ISA/210) mailed on Dec. 18, 2012, by the Japanese Patent Office as the International Searching Authority for International Application No. PCT/JP2012/005596.
(Continued)

*Primary Examiner* — Robert R Raevis
(74) *Attorney, Agent, or Firm* — Buchanan Ingersoll & Rooney PC

(57) ABSTRACT

There is provided a monitoring apparatus including a gas sampling apparatus and a sensor that detects a chemical substance included in gas obtained by the gas sampling apparatus. The gas sampling apparatus includes: an air supplying unit that forms an air curtain to form a space that covers a region to which an object to be monitored is included and which is separated from the outside environment; a sampling unit that extracts the gas inside the separated space; and a diffusion gas supplying unit that supplies, into the separated space, an amount of diffusion gas that is at least equal to the sampled amount of the sampling unit, wherein the sampling unit includes a plurality of sampling nozzles disposed at three-dimensionally different positions inside the separated space.

16 Claims, 5 Drawing Sheets

(51) Int. Cl.
*G01N 15/06* (2006.01)
*G01N 27/62* (2006.01)

(52) U.S. Cl.
CPC ......... *G01N 27/622* (2013.01); *G01N 27/624* (2013.01); *G01N 2001/024* (2013.01); *G01N 2001/028* (2013.01); *G01N 2001/2229* (2013.01); *G01N 2001/2241* (2013.01); *G01N 2001/2285* (2013.01)

(56) References Cited

U.S. PATENT DOCUMENTS

| | | | |
|---|---|---|---|
| 6,334,365 | B1 | 1/2002 | Linker et al. |
| 6,852,539 | B2 * | 2/2005 | Cordery et al. ............ 436/1 |
| 8,377,711 | B2 * | 2/2013 | Henry et al. ............ 436/172 |
| 2003/0043379 | A1 | 3/2003 | Makino et al. |
| 2006/0081073 | A1 | 4/2006 | Vandrish et al. |
| 2006/0243902 | A1 | 11/2006 | Altes Royo |
| 2006/0272393 | A1 | 12/2006 | Jenkins |
| 2009/0084410 | A1 | 4/2009 | Roach et al. |
| 2010/0236341 | A1 | 9/2010 | Martin et al. |
| 2011/0203931 | A1 * | 8/2011 | Novosselov et al. ........ 204/600 |

FOREIGN PATENT DOCUMENTS

| | | |
|---|---|---|
| JP | 6-229889 A | 8/1994 |
| JP | 2003-065910 A | 3/2003 |
| JP | 2006-138731 A | 6/2006 |
| JP | 2007-248114 A | 9/2007 |
| JP | 2008-508693 A | 3/2008 |
| WO | WO 2006/013396 A2 | 2/2006 |

OTHER PUBLICATIONS

International Preliminary Report on Patentability (PCT/IPEA/409) mailed on Sep. 20, 2013, by the Japanese Patent Office as the International Preliminary Examining Authority for International Application No. PCT/JP2012/005596.

Extended European Search Report dated Apr. 1, 2015, issued by the European Patent Office in the corresponding European Application No. 12829348.7. (11 pages).

Supplementary European Search Report dated Apr. 17, 2015, issued by the European Patent Office in the corresponding European Application No. 12829348.7. (1 page).

* cited by examiner

GAS SAMPLING APPARATUS AND MONITORING APPARATUS

TECHNICAL FIELD

The present invention relates to an apparatus for sampling a gas and a monitoring apparatus that uses such gas sampling apparatus.

BACKGROUND ART

Japanese Patent Application No. 2008-508693 (WO2006/013396) discloses an apparatus that measures physical phenomena caused by the difference in ion mobility between substances. Such publication describes in particular an ion mobility spectrometer with an ion filter in the form of at least one ion channel that includes a plurality of electrodes. With this ion mobility spectrometer, it is possible for the filler to selectively input ion types according to the potential applied to the conductive layer that changes over time. Such potential has a drive electric field component and a transverse electric field component, and in a preferred embodiment, the respective electrodes contribute to the generation of both the drive electric field component and the transverse electric field component. Such device can be used even without a drift gas flow. In addition, such publication discloses a micromachining technology for manufacturing a microscale spectrometer for the various applications of a spectrometer.

FAIMS (Field Asymmetric waveform Ion Mobility Spectrometry or DIMS (Differential Ion Mobility Spectrometry)) is known as an example of a technology that measures ion mobility. With FAIMS technology, the chemical substances to be measured are compounds, compositions, molecules and other products that are capable of being ionized, and by using the property whereby ion mobility is unique for each chemical substance, a differential voltage (or "DV", "Dispersion Voltage", "Vd voltage", "electric field voltage", "AC voltage", hereinafter simply "Vf") and a compensation voltage (or "CV", "compensation voltage", "DC voltage", hereinafter simply "Vc") are applied while causing movement within a buffer gas. If Vf and Vc are appropriately controlled, the ionized chemical substance that is the detection target will reach a detector and be detected as a current value.

Accordingly, to use a sensor (ion mobility sensor) that measures ion mobility, it is important to supply chemical substances to be analyzed to the ion mobility sensor under appropriate conditions. This is also the same for other gas analyzing sensors.

One of aspects of the present invention is a gas sampling apparatus including: an air supplying unit that forms an air curtain to form a space that covers a region to which an object to be monitored is included and which is separated from the outside environment; a sampling unit that samples gas inside the separated space; and a diffusion gas supplying unit that supplies, into the separated space, an amount of diffusion gas that is at least equal to a sampled amount of the sampling unit. The sampling unit includes a plurality of sampling nozzles disposed at three-dimensionally different positions inside the separated space.

This gas sampling apparatus uses the sampling unit to sample gas including a chemical substance (target substance) released from the object by the diffusion gas. When doing so, by disposing the plurality of sampling nozzles at three-dimensionally different positions inside the separated space, it is possible to increase the probability of it being possible to sample gas including the target substance, even when the target substance released into the separated space by the diffusion gas is localized somewhere. By such arrangement, it may become possible to sample gas including a high concentration of the target substance, it will be possible to increase the detection precision and reduce the time required for detection.

It is desirable for the gas sampling apparatus to include a first driving unit that moves each of the plurality of sampling nozzles inside the separated space randomly or in accordance with a predetermined algorithm. It is also desirable for the gas sampling apparatus to include a first flowrate control unit that controls a sampled amount of each of the plurality of sampling nozzles randomly or in accordance with a predetermined algorithm. By doing so, it is possible to change the respective sampling conditions of the plurality of sampling nozzles.

It is desirable for the air supplying unit to include an air outlet that forms the separated space above a conveyor that conveys the object, and for the diffusion gas supplying unit to include a diffusion gas outlet that supplies the diffusion gas into the separated space from below the conveyor or along a conveying surface of the conveyor. It becomes easier for constituents released from a target substance included in the object, such as constituents/substances released from foreign materials or abnormalities), to reach the sampling nozzles in a short time. It is also desirable for the gas sampling apparatus to further include a temperature control unit that directly or indirectly heats the object inside the separated space. By heating the object, it is possible to promote releasing of the constituents of the target substance included in the object.

Another aspect of the present invention is a monitoring apparatus including the gas sampling apparatus described above, a sensor that detects at least one chemical substance included in the gas sampled by the sampling unit, and a piping system that connects the gas sampling apparatus and the sensor. It is desirable for the monitoring apparatus to include a heater unit that heats the piping system, which makes it possible to suppress the influence of pollution of the piping system.

It is desirable for the monitoring apparatus to further include a mixer unit that supplies a mixed gas produced by mixing the gas sampled by the sampling unit and a carrier gas to the sensor and also desirable to further include a concentration control unit that controls concentration by feeding back some of the mixed gas as the carrier gas. This makes it possible to easily concentrate the constituents to be detected by the sensor.

It is also desirable for the monitoring apparatus to further include a first feedback control unit that changes respective positions or movements of the plurality of sampling nozzles or a second feedback control unit that changes respective sampled amounts of the plurality of sampling nozzles according to the detection result of the sensor. It is possible to automatically select sampling conditions where the detection sensitivity of the sensor is high and to automatically set the selected sampling conditions.

Although the sensor may be a mass spectrometer, gas chromatography, or the like, an ion mobility sensor that is capable of detecting substances (molecules) in air in real time is preferable.

Yet another aspect of the present invention is a control method of a monitoring apparatus that investigates the state of an object, as examples, whether foreign matter is included in the object, the state of packaging, and the presence/absence of damage. The monitoring apparatus includes: a sampling unit that samples gas inside a space that is separated from the outside environment by an air curtain that covers the object; and a sensor that detects at least one chemical substance included in the gas sampled by the sampling unit, and the sampling unit includes a plurality of sampling nozzles disposed at different positions inside the separated space. The control method includes changing sampling conditions including at least one of a sampled amount, position, and movement of each of the plurality of sampling nozzles.

Changing the sampling conditions may include changing sampling conditions of the plurality of sampling nozzles randomly or in accordance with a predetermined algorithm. Also, changing the sampling conditions may include changing the sampling conditions of the plurality of sampling nozzles in accordance with a detection result of the sensor.

DETAIL DESCRIPTION

Figure 1:
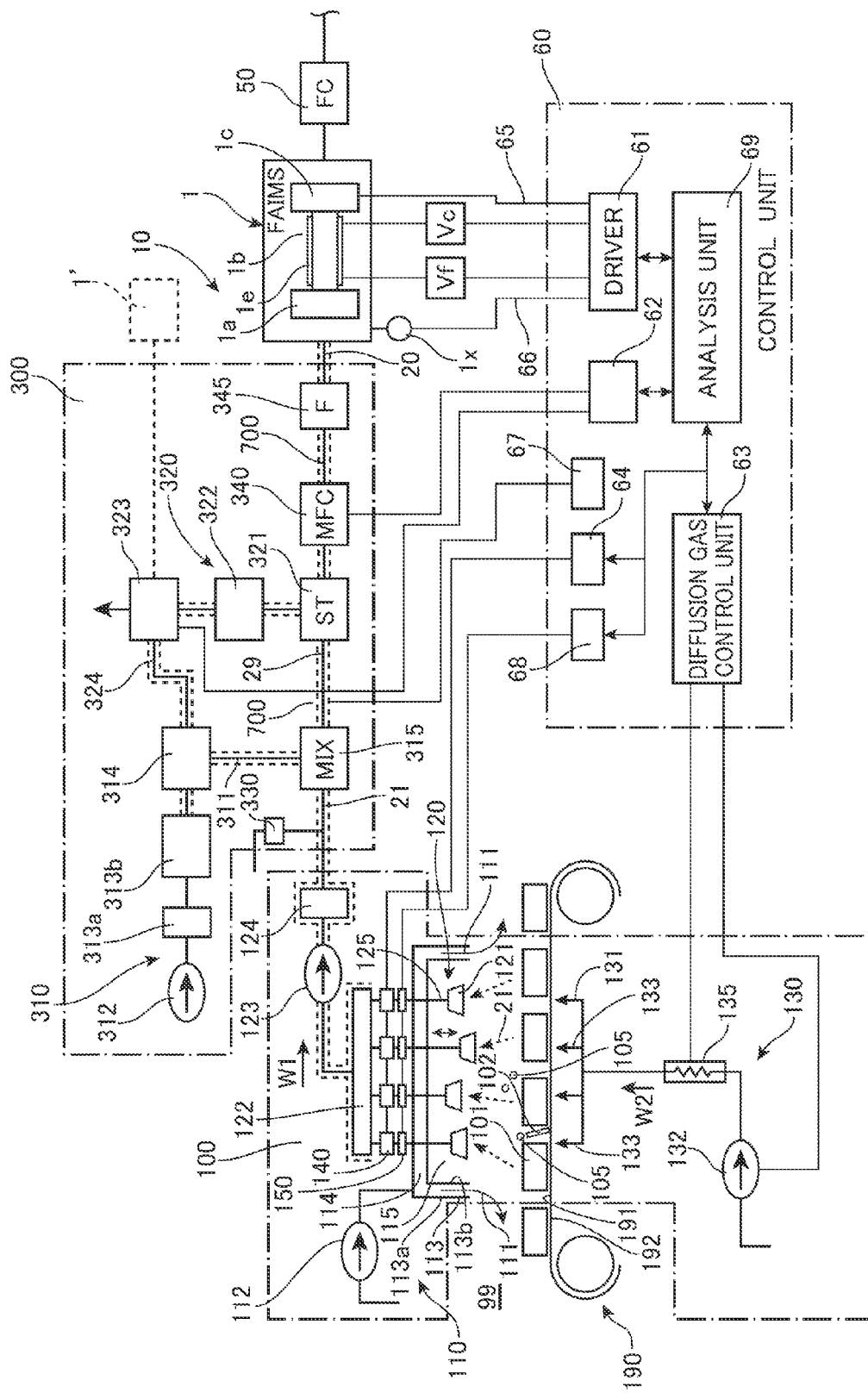
FIG. 1 is a block diagram showing a monitoring apparatus.

FIG. 1 shows an overview of a monitoring apparatus equipped with an ion mobility sensor. Such monitoring apparatus (testing apparatus, inspection apparatus, detection apparatus, analysis apparatus) 10 includes, from an upstream side thereof, a gas sampling apparatus 100 that samples a gas ("target gas" or "sampling gas", "gas sample") 21 to be detected which includes a chemical substance (target substance) 105 released from products (objects) 101 and 102 to be monitored (tested, inspected, investigated), a preparation unit 300 that prepares a detection gas 20 that is to be supplied to an ion mobility sensor (sensor) 1, a flow controller 50 that controls the amount of gas that flows through the sensor 1, and a control unit 60 that controls the monitoring apparatus 10.

One example of the ion mobility sensor 1 according to the present embodiment is a FAIMS (Field Asymmetric Waveform Ion Mobility Spectrometry or DIMS (Differential Ion Mobility Spectrometry)). The sensor 1 includes an ionizing unit 1a that ionizes a target chemical substance (or "target substance" or "target chemical"), a drift chamber 1b that transfers the ionized target substance while applying the effects of an electric field, and a detector 1c that detects the ionized measured object (the electric charge to be measured) that has passed through the drift chamber 1b. In the drift chamber 1b, the electric field generated by the electrodes 1e and controlled by software changes between positive and negative with a specified cycle, and due to the filtering effect of such electric field, chemical substances that are the detection targets are selected, and collide with the detector 1c and are measured as electric currents in a short period, for example, at msec level.

One example of the sensor (FAIMS) 1 is a sensor made by Owlstone, with $Ni_{63}$ (a 555 MBq β source, 0.1 μSv/hr) being used in the ionizing unit 1a. The chemical substances that can be ionized by the ionizing unit 1a have an ionization binding energy of 67 KeV or below, which means that it is possible to detect and analyze a wide range of chemical substances. Devices that use UV (ultraviolet), devices that use corona discharge, and the like are being investigated as the ionizing unit 1a.

The control unit (control apparatus) 60 may be a computer equipped with hardware resources including a CPU and a memory, or may be a semiconductor device such as a system LSI. The control apparatus 60 includes a driver (driver program, program product) 61 that controls the sensor 1 and an analysis unit 69 that controls, via the driver 61, the measurement conditions of the sensor 1 and analyzes the measurement results of the sensor 1 obtained via the driver 61. The measurement conditions are sent from the driver 61 to the sensor 1. The measurement conditions include the field voltage Vf (hereinafter simply "voltage Vf") and the compensation voltage Vc.

The driver 61 acquires the measured data (IMS data) 65 from the sensor 1. One example of the IMS data 65 is a spectrum expressed by a current (the current detected by a detection apparatus 1c) I that changes corresponding to variations in the compensation voltage Vc at a specified voltage Vf. The IMS data 65 may be data produced by sampling (extracting) feature points of the spectrum described above or may include spectra of a plurality of voltages Vf. The driver 61 also acquires information 66 on the measurement environment of the sensor 1. The measurement information 66 includes temperature, humidity, pressure, flow rate, and the like, with a sensor 1x for detecting such information being provided in the sensor 1.

In the present embodiment, the gas sampling apparatus 100 that extracts the sampling gas (or "sample gas") to be monitored or tested obtains the sampling gas 21 from a conveyor 190 that conveys products of one or a plurality of types. The sampling gas 21 is sent via the preparation unit 300 to the sensor 1, and by measuring and/or detecting the target substance 105 included in the sampling gas 21, it is possible to determine the product 101 conveyed by the conveyor (belt conveyor) 190, to determine (detect) the presence or absence of damage to the product 101, and/or to determine (detect) foreign matter 102 that has the possibility of being included in the product 101.

The gas sampling apparatus 100 includes an air supplying unit 110 that forms an air curtain 111 to cover a region including the objects 101 and 102 to form a space (sampling space) 115 that is separated from the outside world (outside environment) 99, a sampling unit 120 that obtains the gas inside the sampling space 115, that is, the sampling gas 21, and a diffusion gas supplying unit 130 that supplies, into the sampling space 115, an amount W2 of diffusion gas 131 that is at least equal to the sampled amount W1 of the sampling unit 120.

The air supplying unit 110 includes a fan 112 that supplies air 111 and a hood 113 that blows out the air 111 for an air curtain in the periphery of the sampling space 115. The hood 113 has a double-wall construction including an upper housing 113a and a lower housing 113b and the air 111 for the air curtain is supplied to specified positions via the space 114 between the housings 113a and 113b.

The sampling unit 120 includes a plurality of sampling nozzles 121 disposed at three-dimensionally different positions inside the sampling space 115, a sampling chamber 122 to which the plurality of sampling nozzles 121 are connected, a sampling pump 123 that draws the sampling gas 21 via the sampling chamber 122, and a sampling buffer 124. The sampling pump 123 is typically a diaphragm-type pump that has a Teflon (registered trademark) coating, and by providing the sampling buffer 124, pulsation of the sampled sampling gas 21 is suppressed.

The respective sampling nozzles 121 typically extend in cone or trumpet shapes in the direction of the conveying surface 191 of the conveyor 190, that is, the product 101 or 102 conveyed by the conveyor 190. The plurality of sampling nozzles 121 are disposed at three-dimensionally different positions inside the sampling space 115. That is, inside the sampling space 115, the plurality of sampling nozzles 121 are disposed in a two-dimensional matrix along the conveying surface 191 of the conveyor 190, and by changing the distance between the respective sampling nozzles 121 and the conveying surface 191, the plurality of sampling nozzles 121 are disposed at three-dimensionally different positions.

The respective sampling nozzles 121 are connected via sampling pipes 125 to the sampling chamber 122. The gas sampling apparatus 100 further includes a driving unit 140 that dynamically changes the lengths of the respective sampling pipes 125 and a flowrate control unit 150 that controls the pressure drop in the respective sampling pipes 125 to control the flowrates of the sampling gas 21 flowing in the sampling pipes 125.

The diffusion gas supplying unit 130 includes a diffusion gas supplying pump 132, a plurality of supplying nozzles 133 that blow out the diffusion gas (dispersion gas) 131 inside the sampling space 115 from below the conveyor 190 and a heater 135 that heats the diffusion gas 131. If a belt 192 that constructs the conveying surface 191 of the conveyor 190 is capable of transmitting gas, such as by being porous or mesh-like, the diffusion gas 131 is supplied inside the sampling space 115 from below the belt 192. On the other hand, if the belt 192 is not capable of transmitting gas, the diffusion gas 131 is supplied from the supplying nozzles 133 disposed in the periphery of the conveying surface 191 inside the sampling space 115 toward the conveying surface 191 or along the conveying surface 191.

Figure 2:
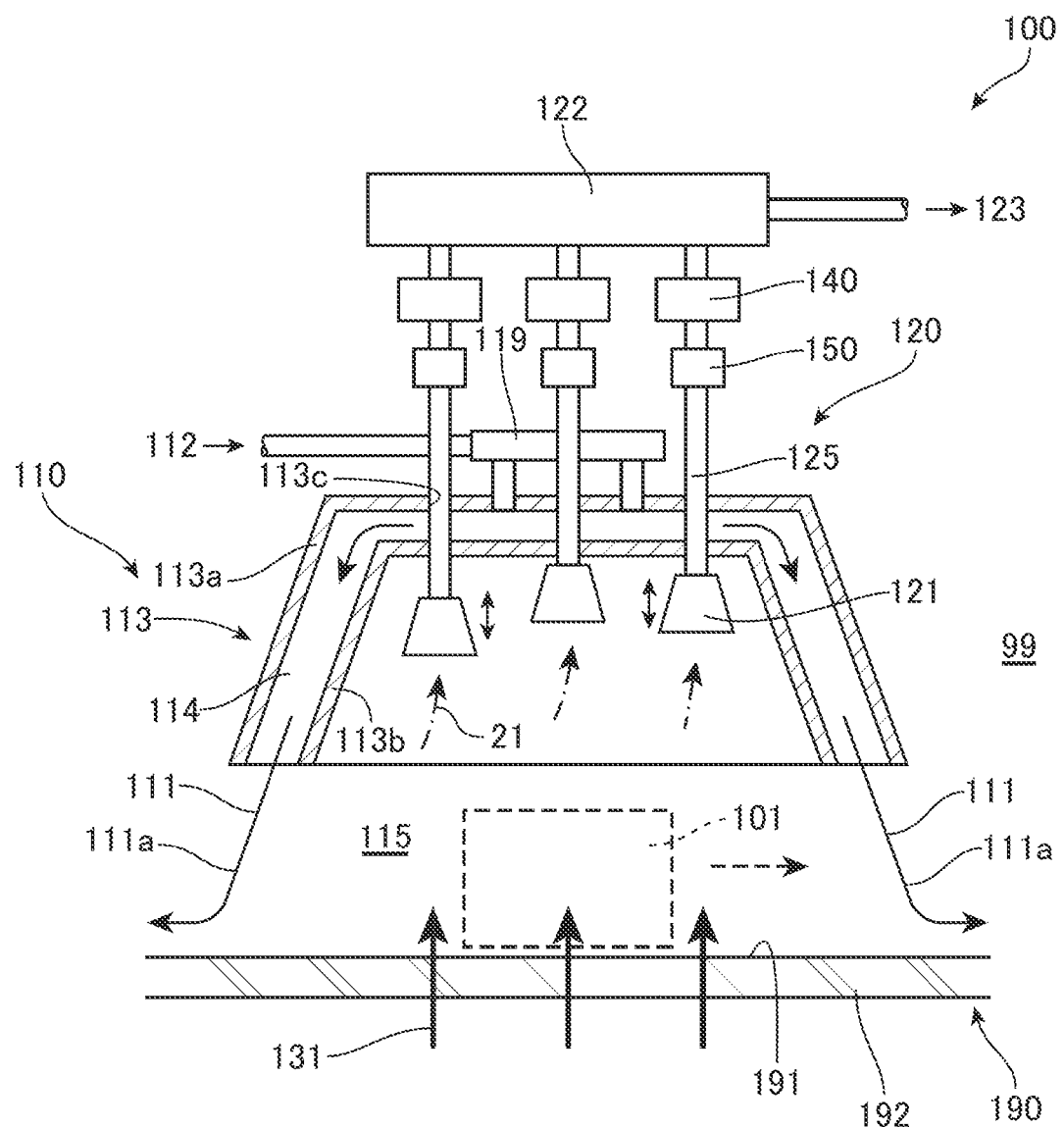
FIG. 2 shows an arrangement of a gas sampling apparatus.
Figure 3:
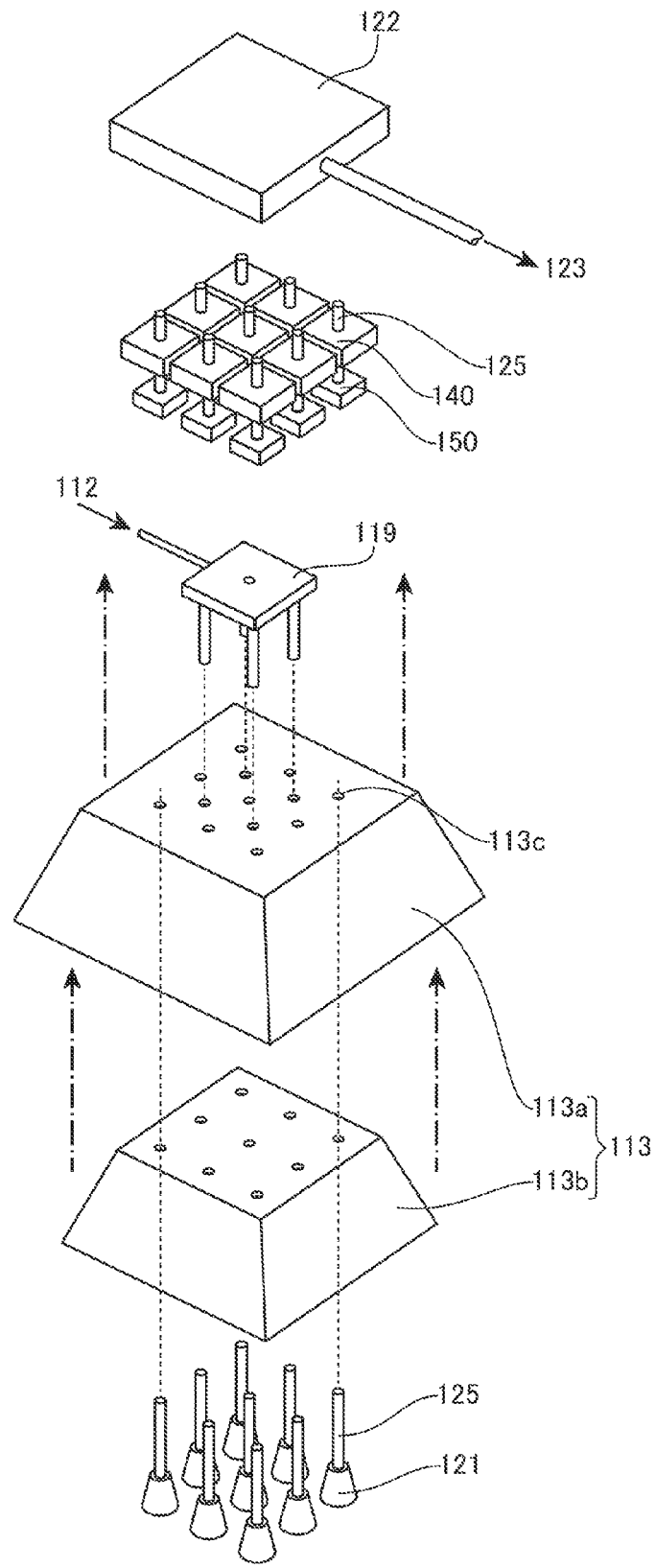
FIG. 3 is an exploded diagram showing an arrangement of a hood.

FIG. 2 schematically shows, by way of a cross-sectional view, how the sampling space 115 is formed and how the sampling gas 21 is drawn. FIG. 3 is an exploded view showing the overall construction of the hood 113. In the gas sampling apparatus 100, the air 111 that has been supplied from the supply pump 112 is supplied via a supply chamber 119 to the hood 113 that in the form of a truncated quadrangular pyramid that is somewhat wider at the bottom. The air 111 is guided over the conveyor 190 by a supply path 114 of the hood 113, and the sampling space 115, which is separated from the outside environment 99 in four directions by the air curtain 111a formed by the air 111 blown out from the hood (air outlet) 113, is formed above the conveyor 190.

Accordingly, once the object 101 has been conveyed into the sampling space 115 by the conveyor 190, the region including the product 101 will be shut out from the outside environment 99. This means that if a chemical substance that is the cause of an odor and/or a chemical substance which does not have an odor but has different constituents to the constituents included in air is released from the object 101, it will be possible to sample sampling gas 21 that includes such substances separately to the air in the outside environment 99.

The gas sampling apparatus 100 includes nine sampling nozzles 121 that are disposed inside the sampling space 115. The number of the sampling nozzles 121 is not limited to nine and may be eight or less or ten or more. It is preferable to dispose an appropriate number of sampling nozzles 121 in keeping with the volume of the sampling space 115 and the like. The nine sampling nozzles 121 are two-dimensionally disposed in a 3×3 matrix (array) across the conveying surface 191. Holes 113c for passing through the sampling pipes 125 that connect the respective sampling nozzles 121 to the sampling chamber 122 are provided in the respective housings 113a and 113b of the hood 113.

If the respective distances between the sampling nozzles 121 and the conveying surface 191 differ, the sampling nozzles 121 as a whole will be disposed at three-dimensionally different positions inside the sampling space 115. The respective sampling pipes 125 are extended and retracted by the driving unit 140 so that the respective distances between the respective sampling nozzles 121 and the conveying surface 191 dynamically change. One example of the driving unit 140 is a combination of an extending/retracting coupling and an actuator that extends and retracts the extending/retracting coupling. One example of the actuator is an air cylinder.

Accordingly, the positions (heights) of the sampling nozzles 121 inside the sampling space 115 can be freely adjusted. The control unit 60 includes a nozzle position control function 64 that controls the respective positions of the sampling nozzles 121 via the respective driving unit 140 and controls the sampling conditions of the respective sampling nozzles 121. The nozzle position control function 64 is capable of shifting the positions of the respective sampling nozzles 121 according to a specified algorithm and is also capable of randomly shifting the positions using random numbers.

In addition, the gas sampling apparatus 100 includes the flowrate control unit 150 that controls the pressure drop in the respective sampling pipes 125. One example of the flowrate control unit 150 is a flowrate control valve and it is possible to dynamically and freely control the amount of gas 21 that is sampled by the respective sampling nozzles 121. The flowrate control unit 150 is also capable of setting the sampled amount of any of the sampling nozzles 121 at zero.

The control unit 60 includes a nozzle flowrate control function 68 that controls the sampling conditions of the respective sampling nozzles 121 by separately controlling the sampled amount of the sampling nozzles 121 via the respective flowrate control unit 150. The nozzle flowrate control function 68 is capable of changing the flowrates of the respective sampling nozzles 121 according to a specified algorithm and is also capable of randomly changing the flowrates using random numbers.

The control unit 60 is a programmable control apparatus including a CPU and a memory, for example. The functions realized in the control unit 60 can be recorded on an appropriate recording medium as a program (program product) and/or can be provided via a network.

The control unit 60 also includes the diffusion gas control function 63 that controls the flowrate and temperature of the diffusion gas 131 that is the source of the sampling gas 21 acquired by the sampling nozzles 121. The diffusion gas control function 63 controls the flowrate by controlling the rotational speed of a diffusion gas supplying pump ("supply fan", "supply blower") 132. It is also possible to use another flowrate control means, such as a damper. The same applies to other flowrate control. It is also possible to provide a flowrate control unit for each blowing (outlet) nozzle 133 of the diffusion gas 131 and to control the amount of air blown out from each outlet nozzle 133.

The diffusion gas control function 63 also controls the heater 135 attached to a diffusion gas supplying line to control the temperature of the diffusion gas 131. A typical example of the diffusion gas 131 is air (atmospheric air). It is desirable for there to be little variation in time in the constituents of the diffusion gas 131 and to not include chemical substances related to the substances 101 and 102 to be monitored and/or other chemical substances that produce noise. Accordingly, it is desirable for the diffusion gas 131 to be clean, dry air that has been supplied via an appropriate adsorbent such a silica gel or a molecular sieve, a hydro carbon filter, or the like. The diffusion gas 131 does not need to be atmospheric air and may be a purified air, an inert gas such as nitrogen gas, or the like.

The preparation unit 300 adjusts the concentration of the sampling gas 21 sampled by the gas sampling apparatus 100. The preparation unit 300 includes a carrier gas supplying unit 310, a concentration adjusting unit 320, a mass flow controller (MFC) 340, and a particle filter 345. The carrier gas supplying unit 310 includes a supplying pump (supplying fan) 312, a hydro carbon filter 313a, a pressure regulator 313b, and a mixer 314 that mixes with a feedback gas 324, described later. The preparation unit 300 includes a gas mixer 315 that mixes the carrier gas 311 produced by the carrier gas supplying unit 310 and the sampling gas 21 supplied from the gas sampling apparatus 100.

A diluted gas 29 is produced by mixing the sampling gas 21 and the carrier gas 311 and flowrate control over some of the gas 29 is carried out by the MFC 340, so that a fixed flowrate of test gas (sampling gas) 20 is supplied via the particle filter 345 to the sensor 1. The remainder (exhaust) of the diluted gas 29 is supplied to the concentration adjusting unit 320. The concentration adjusting unit 320 includes a pre-concentrating split tee 321 that extracts (exhausts) some of the diluted gas 29, a pressure controller 322 that controls the pressure on the exhaust side, and a bypass control unit 323 that controls the flowrates of the gas to be exhausted and the gas (feedback gas) 324 to be fed back to the carrier gas 311 and exhausts the remainder. The bypass control unit 323 may supply all or some of the gas to be exhausted to a reserve sensor 1'. The reserve sensor 1' has the same construction as the main sensor 1 and has applications such as a mirror sensor for the main sensor 1, standby purposes, and calibration purposes.

By returning all or some of the diluted gas 29 to the carrier gas 311 via the concentration adjusting unit 320, it is possible to raise the concentration of the sampling gas 21 in the diluted gas 29 and adjust the concentration of the test gas 20 to be detected. If the amount of the sampling gas 21 obtained (sampled) by the gas sampling unit 100 is large, it is possible to provide an exhaust system 330 upstream of the gas mixer 315 that mixes with the carrier gas 311, to control the amount of the sampling gas 21 supplied to the preparation unit 300, and to control the amount of sampling gas 21 included in the diluted gas 29.

The concentration and flowrate of the test gas (monitoring gas) 20 are carried out by mainly controlling the MFC 340 and the bypass control unit 323 using the flowrate control function 62 of the control unit 60. The mass flow controller (MFC) 340 is a device that measures the mass flow rate of a fluid and carries out flowrate control, with a digital MFC being used in the monitoring apparatus 10. When measuring the flowrate of a fluid, volume flow and mass flow are mainly used. With volume flow, changes in volume will occur due to changes in the environmental temperature and used pressure of the fluid being measured, and therefore to measure the flow rate accurately, correction is carried out in accordance with such changes. With mass flow, by measuring the mass (weight) of the fluid, it is not necessary to correct changes in the usage conditions. The MFC 340 is a well-known device as a flowrate control mechanism for a process, such as a semiconductor process, where highly precise measurement and control of flowrate are required.

In addition, the analyzing apparatus 10 includes a heater (trace heater) 700 that heats the pipe that extends from the sampling chamber 122 to the sensor 1, that is the pipes that supply the sampling gas 21, the diluted gas 29, and the test gas 20, a pipe that supplies the filtered carrier gas 311, and the pipe that supplies the feedback gas 324 of the concentration adjusting unit 320. The trace-heated range is shown by the broken lines in FIG. 1. The pipes that are trace-heated are coated with Teflon (registered trademark) or the like, for example, and by heating to around 30 to 80° C., it is possible to prevent various constituents from adhering to the pipes and causing noise. The control unit 60 includes a function 67 for controlling the temperature of the heat trace.

There are a number of problems when chemical substances derived from objects (things, materials, commodities, products, and living bodies (animals and humans)) are sampled and monitored (detected, tested, inspected) in the atmosphere. First, various chemical substances are included in the atmosphere for a variety of reasons. In particular, in a factory or other manufacturing facility, a great variety of compositions and molecules are released from machines, floors, walls, and the like, and the amount (concentration) of such compositions and molecules that are released will vary from moment to moment due to a variety of reasons. The presence of such chemical substances as a background is an obstruction when detecting constituents in minute amounts (trace constituents).

One example of where detection of constituents in minute amounts (minor components, trace constituents) is required is when detecting foreign matter that can be mixed into foodstuffs or can cause pollution of foodstuffs, such as plastic, hair, and agricultural chemicals. Another example of where detection of constituents in minute amounts is required is when detecting problems with food products, for example when detecting improper sealing of canned or packaged goods, and discrepancies between packaged foodstuffs and the written content of a label. Yet another example of where detection of trace constituents is required is when detecting hazardous materials (such as explosives) included in transported goods and detecting whether people boarding a means of transport, such as an airplane, are carrying hazardous materials. In any of such cases, it is preferable to exclude the influence of background constituents.

Due to the chemical substances in the atmosphere, there is always variation in the background, and since a large number of volatile compounds are included, it is almost impossible to know in advance all of the chemical substances that are included in the atmosphere. Such chemical substances are the background when detecting a target using an ion mobility sensor, and have a high probability of obstructing tests and monitoring. Although such a background can be processed to an extent by software processing, it is difficult to completely remove the background, with software processing also being facilitated by the presence of little background.

The monitoring apparatus 10 includes an RCSS (Real Time Chemical Sampling and Background Suppression System) function. The RCSS first seals the periphery of the products 101 and 102 to be monitored from the outside environment using the air curtain 111 to form the space for sampling (sampling space) 115. In the example described above, a head space 115 for sampling is formed above the conveyor 190. When monitoring in atmospheric air, it is important to form such a head space 115. By forming the head space 115 that has a certain volume and does not directly contact the outside environment 99 due to the air curtain 111, molecules of the target substance 101 or 102 will react or molecules of the target substance 101 or 102 will be released inside such separated space 115, which increases the concentration of the chemical substances to a detectable level. It is also easy to stabilize environmental conditions, such as temperature, humidity, flowrate, and pressure, inside the space 115 that is separated from the outside 99.

Inside the separated space 115, it is also possible to prevent dispersion of the molecules into a wider space by Brownian motion. Accordingly, by disposing the sampling nozzles 121 inside the separated sampling space 115, it is possible to guide molecules derived from the target substance 101 or 102 to the sampling nozzles 121 and sample the molecules. In addition, since the separated sampling space 115 can be regarded as a space with a fixed volume, it is also possible to define the concentration. This means that from the concentration of the molecules (chemical substances) sampled at the sampling nozzles 121, it is possible to grasp, the concentration of the molecules derived from the target substance 101 or 102, the cause of such molecules being released, the amount of foreign matter, the concentration of a pollutant material, and the extent of damage of a product.

By three-dimensionally disposing the plurality of the sampling nozzles 121 in the sampling space 115, it is possible to sample target molecules 105 that are trapped anywhere in the sampling space 115 at a variety of positions, which makes it possible to carry out sampling more efficiently and more reliably even when the target molecules 105 are not uniformly distributed in the sampling space 115.

Also, the monitoring apparatus 10 investigates the test objects (samples) 101 and 102 conveyed by the conveyor 190 in real time. As one example, the samples 101 and 102 move at 10 to 20 m per minute. If the width of the sampling space 115 is 20 cm, the samples 101 and 102 will cross the sampling space 115 in a time of around 500 ms. Accordingly, it is necessary to analyze and detect the test gas 20 including the sampling gas 21 at the sensor 1 in an extremely short time. For this reason, the sensor 1 is optimized to carry out not a positive-negative scan but instead a positive-positive scan, the detection time (sampling time) of one iteration is reduced from 2 ms to 1 ms and the number of steps (CV steps) in which the value of Vc is changed is reduced from 512 to 50.

It is also effective to introduce (supply) the diffusion gas (dispersion gas) 131 into the sampling space 115 from a different direction to the air 111 for the air curtain. First, by introducing, into the sampling space 115, an amount W2 of the diffusion gas 131 that is equal to or larger than an amount of gas W1 extracted by the sampling unit 120, it is possible to prevent the sampling space 115 from becoming under negative pressure and thereby suppress mixing of the air 111 for the curtain into the sampling space 115. As one example, the supplied amount of air 111 for the air curtain is 10 to 20 SLPM (standard liters/minute) and the sampled amount W1 of the sampling gas 21 is 10 to 2000 milliliters/minute. Accordingly, it is desirable for the amount W2 of the diffusion gas 131 to be around 10 to 2000 milliliters/minute. Also, although an example where the number of sampling nozzles 121 is nine has been described above, it is even more effective for the number to be ten to twenty.

The diffusion gas 131 also includes a function for replacing external air that is trapped in cavities in the samples 101 and 102 and may form the background. As one example, for a foodstuff such as potato chips, even when passing the air curtain 111*a*, external air will be trapped between stacked chips and in convex and concave parts of the potato chips, forming a background. The diffusion gas 131 replaces the trapped external air and, by contacting or reacting with the samples 101 and 102 to be monitored, efficiently releases and disperses the molecules 105 that are the target for detection into the sampling space 115. Accordingly, by introducing the diffusion gas 131 into the sampling space 115, releasing secondary outside air and/or releasing other gas that may form a background are rapidly done, weakening the influence of such gases and promoting the releasing of the molecules 105 that are the target for detecting. This means that the sensitivity of the monitoring apparatus 10 is increased, which makes real-time detection possible.

To improve the detection performance of the monitoring apparatus 10, it is desirable for the diffusion gas 131 to be air that is as dry and clean as possible. Also, when monitoring the samples 101 and 102 conveyed by the conveyor 190, it is effective to dispose the blowing nozzles (outlet nozzles) 133 of the diffusion gas 131 so as to supply or blow the diffusion gas 131 from below the conveyor 190 or along the conveying surface 191 of the conveyor 190. The gas in the periphery of the samples 101 and 102 on the conveyor 190 is rapidly replaced with the diffusion gas 131 which means that it is possible to efficiently produce and extract (sample) the sampling gas 21 including the molecules 105 derived from the samples 101 and 102.

In addition, it is possible to direct the flow of the sampling gas 21 toward the sampling nozzles 121 positioned above the conveyor 190 on the opposite side to the supplying nozzles 133, which makes it possible to efficiently collect the sampling gas 21. Also, even if a sample 101, such as potato chips, is being conveyed in a stacked state, by supplying the diffusion gas 131 along the conveying surface 191 and/or supplying the diffusion gas 131 from the opposite side of the belt 192, it is possible to release, into the sampling space 115, molecules 105 derived from a lower part of the sample 101 and molecules 105 derived from foreign matter 102 that is hidden by an upper part of the sample 101 and cannot be seen and to recover such molecules 105 at the sampling unit 120.

In addition, at the monitoring apparatus 10, the plurality of sampling nozzles 121 of the gas sampling apparatus 100 are respectively moved by the driving unit 140 randomly or according to a predetermined algorithm inside the separated sampling space 115. By moving each of the plurality of sampling nozzles 121 that are disposed in three dimensions up and down, it is possible to change the three-dimensional pattern of the sampling nozzles 121 together with the passing of time. This means that it is possible to sample the sampling gas 21 including the target molecules 105 even more reliably, even if the target molecules are blown to a localized position of the sampling space 115 or the concentration inside the sampling space 115 is unbalanced.

The nozzle position control function 64 may include a function ("first feedback control unit") that controls the driving unit 140 so as to change the positions or movement of the plurality of sampling nozzles 121 according to the detection result of the sensor 1. The detection result of the sensor 1 is provided from the analysis unit 69. When a particular flow or distribution is produced inside the sampling space 115, by setting the sampling nozzles 121 at positions where the concentration of the target molecules 105 is high, it is possible to further increase the detection sensitivity of the monitoring apparatus 10. Also, when a certain detection sensitivity is not obtained, by changing the positions of the sampling nozzles 121 randomly or based on a predetermined algorithm, it may be possible to automatically discover a pattern that obtains a high detection sensitivity. In addition, the form and/or distribution of the samples 101 may be determined using image recognition or the like and the plurality of sampling nozzles 121 may be automatically moved so as to produce a nozzle layout which is likely to have the highest detection sensitivity.

Also, the gas sampling apparatus 100 of the monitoring apparatus 10 further includes the flowrate control unit 150 that controls the respective sampled amounts of the plurality of sampling nozzles 121. Accordingly, out of the sampling nozzles 121 that are three-dimensionally disposed, it is possible to increase the sampled amounts of nozzles 121 that are sampling gas 21 with a high concentration of the target molecules 105 and to reduce the sampled amounts of other nozzles 121, thereby extracting sampling gas 21 with even higher detection efficiency.

The nozzle flowrate control function 65 controls the respective sampled amounts of the plurality of sampling nozzles 121 randomly or in accordance with a predetermined algorithm and is capable of controlling the sampled amounts of the respective nozzles 121 so as to sample high-concentration sampling gas 21 with the highest efficiency. The nozzle flowrate control function 65 may also include a function (second feedback control unit) that controls the flowrate control unit 150 so as to automatically change the sampled amounts of the plurality of sampling nozzles 121 in accordance with the detection result of the sensor 1.

By changing the sampled amounts of the sampling nozzles 121 together with the three-dimensional layout pattern of the sampling nozzles 121, there is an increase in the options for selecting a patterns for sampling the sampling gas 21 from inside the sampling space 115, which makes it possible to automatically discover an optimal sampling pattern (sampling conditions), to heuristically discover an optimal sampling pattern, and to learn and predict based on such experiences. Together with or separately to the layout of nozzles, it is also possible to determine the form or distribution of the sample 101 by image recognition or the like and to automatically vary the balance of nozzle flowrates to a balance likely to produce the highest detection sensitivity.

Also, the gas sampling apparatus 100 includes a heater 135 that heats the diffusion gas 131 and by heating the samples 101 and 102 of the sampling space 115 indirectly via the diffusion gas 131, the releasing of molecules 105 derived from the sample 101 or 102 into the sampling space 115 is promoted. It is also possible to heat the belt 192 of the conveyor 190 using a heater or the like to directly or actively heat the samples 101 and 102.

The heating temperature is a range that does not affect the quality of the samples. Depending on the temperature, chemical substances released from a proper sample 101 will form a background, which for example has the possibility of a drop in the detection sensitivity when chemical substances released for the foreign matter 102 are the target molecules 105. The diffusion gas control function 63 may also include a function that controls the temperature for heating the samples 101 and 102 based on the detection result of the sensor 1.

The preparation unit 300 of the monitoring apparatus 10 includes a mixer unit 315 that supplies mixed gas 29 produced by mixing the gas 21 obtained by the sampling unit 120 and a carrier gas 311. If the gas flowrate detected at the sensor 1 is insufficient or the concentration is too high, adjustment is carried out using the carrier gas 311. The preparation unit 300 includes a concentration adjusting unit 320 and is capable of feeding back part of the mixed gas 29 as the carrier gas 311 to control the concentration. With the ion mobility sensor 1, since the current value will be exceeded if the concentration is too high, there is the possibility of a drop in detection sensitivity, while if the concentration is too low, there is the possibility that detection will not be possible. Accordingly, making it possible to adjust the concentration of the test gas 20 supplied to the sensor 1 is effective in raising the detection sensitivity of the sensor 1.

Figure 4:
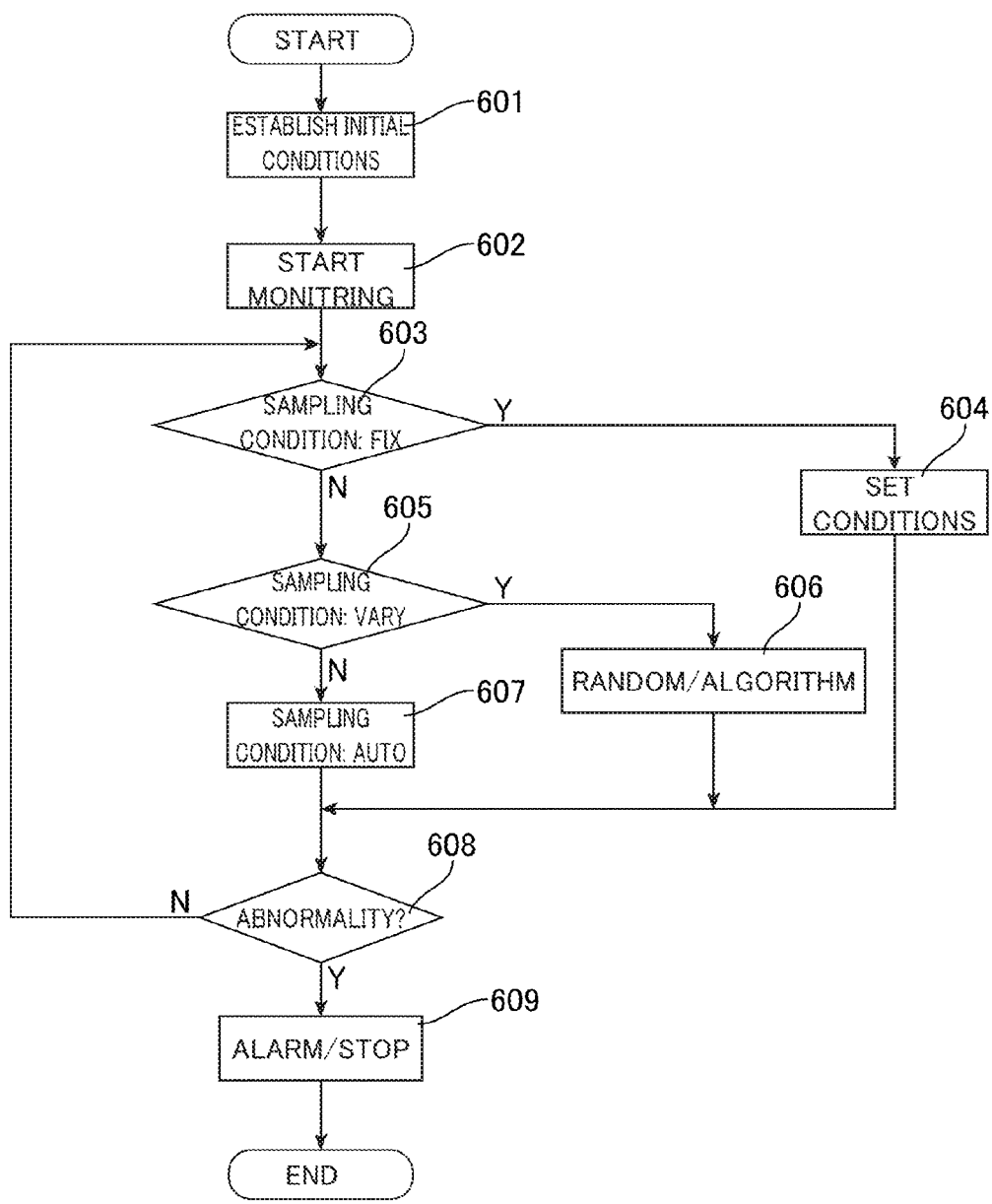
FIG. 4 is a flowchart showing an overview of the investigating procedure by the monitoring apparatus.

FIG. 4 shows an overview of a process for monitoring (investing) an object using the monitoring apparatus 10 by way of a flowchart. In step 601, the flow of the air curtain 111 is established and when the initial conditions for starting monitoring, such as the establishment of the flow of the diffusion gas 131, are satisfied, in step 602, the conveyor 190 is moved and the monitoring starts. In step 603, if the sampling condition is set as a fix condition, in step 604 sampling conditions such as the nozzle positions and sampled amounts are set at values (conditions) set in advance and the sampling gas 21 is sampled. In step 605, if the sampling condition is set as variable, in step 606 the nozzle positions, sampled amounts and the like are shifted randomly or according to a predetermined algorithm with an appropriate cycle and the sampling gas 21 is sampled. When the sampling condition is set as an automatic, in step 607 the analysis unit 69 automatically changes the nozzle positions, sampled amounts, and the like via the nozzle position control function 64 and the nozzle flowrate control function 65 so as to optimize the sampling conditions based on the detection result of the sensor 1.

In step 608, if the sensor 1 has detected molecules 105 that may cause or result of an abnormality in the sampling gas 21, in step 609 an alarm is outputted and/or the conveyor 190 is caused to come to an emergency stop so as to specify or make removal possible for the object 101 for which the abnormality was detected.

Figure 5:
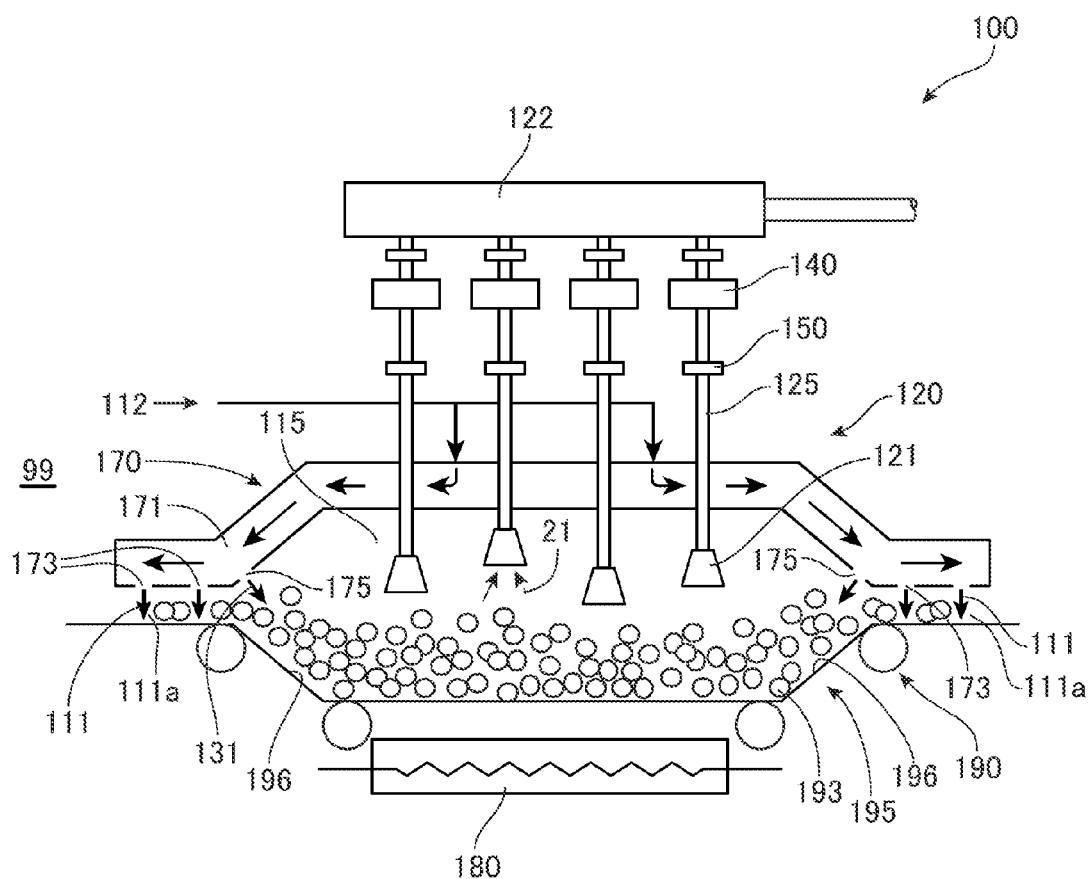
FIG. 5 is a diagram showing a different example of a gas sampling apparatus.

FIG. 5 shows a different example of the gas sampling apparatus 100. The gas sampling apparatus 100 is attached to a pot-shaped position 195 midway on the conveyor 190, with a hood 170 for forming the sampling space 115 being disposed above the pot 195. The hood 170 also serves as a path 171 that supplies the air 111 that forms the air curtain 111*a*. Blowholes (air outlets) 173 for the curtain air 111 are provided at an end portion of the hood 170 so that the air curtain 111*a* that separates the sampling space 115 from the outside environment 99 is formed. In addition, the hood 170 also serves as a path that supplies the dispersion air 131 as the diffusion gas, and nozzles 175 that discharge the diffusion gas 131 into the sampling space 115 along an inclined surface 196 of the pot 195 are formed on the inside of the hood 170. In addition, a heater 180 for heating the sample 193 inside the pot 195 is provided below the pot 195.

This gas sampling apparatus 100 is also provided with a plurality of sampling nozzles 121 that are three-dimensionally disposed inside the sampling space 115, and such sampling nozzles 121 are moved up and down by the driving unit 140, with the sampled amounts being automatically adjusted by the flowrate control unit 150. Accordingly, with this gas sampling apparatus 100 also, it is possible to sample the gas 21 from the sampling space 115 in the same way as the gas sampling apparatus described above.

Note that although a monitoring apparatus that uses an ion mobility sensor as the sensor 1 that analyzes the sampling gas 21 has been described above, it is also possible to use ion chromatography, gas chromatography, or another gas sensor such as that uses optics or vibrations.

The invention claimed is:

1. A gas sampling apparatus comprising:
   a support surface to support an object to be monitored;
   an air supplying unit that forms an air curtain to form a separated space that covers a region to which the object to be monitored is included and which region is separated from outside environment by the air curtain;
   a sampling unit that samples gas inside the separated space; and
   a gas supplying unit that supplies, into the separated space, an amount of gas that is at least equal to a sampled amount of the sampling unit,
   wherein the sampling unit includes a plurality of sampling nozzles, wherein each of the sampling nozzles is disposed over a different portion of the support surface, and the sampling nozzles are disposed at different distances from the support surface, the plurality of sampling nozzles being disposed inside the separated space.

2. The gas sampling apparatus according to claim 1, further comprising a first driving unit that moves each of the plurality of sampling nozzles inside the separated space randomly or in accordance with a predetermined algorithm on a cyclical basis.

3. The gas sampling apparatus according to claim 1, further comprising a first flowrate control unit that controls a sampled amount of each of the plurality of sampling nozzles randomly or in accordance with a predetermined algorithm on a cyclical basis.

4. The gas sampling apparatus according to claim 1,
   wherein the surface is a surface of a conveyor that conveys the object, and the air supplying unit includes an air outlet that forms the separated space above the conveyor surface, and
   the gas supplying unit includes a gas outlet that supplies the gas into the separated space from below the conveyor or along the conveying surface.

5. The gas sampling apparatus according to claim 1, further comprising a temperature control unit that directly or indirectly heats the object inside the separated space.

6. A monitoring apparatus comprising:
   the gas sampling apparatus according to claim 1;
   a sensor that detects at least one chemical substance included in the gas sampled by the sampling unit; and
   a piping system that connects the gas sampling apparatus and the sensor.

7. The monitoring apparatus according to claim 6, further comprising a heater that heats the piping system.

8. The monitoring apparatus according to claim 6, further comprising a mixer that supplies a mixed gas produced by mixing the gas sampled by the sampling unit and a carrier gas to the sensor.

9. The monitoring apparatus according to claim 8, further comprising a concentration control unit that controls a concentration of the mixed gas by feeding back some of the mixed gas as the carrier gas.

10. The monitoring apparatus according to claim 6, further comprising a first feedback control unit that changes respective positions or movements of the plurality of sampling nozzles according to a detection result of the sensor so as to increase a concentration of target chemical substance in the gas sampled.

11. The monitoring apparatus according to claim 10, further comprising a second feedback control unit that changes respective sampled amounts of the plurality of sampling nozzles according to the detection result of the sensor so as to increase a concentration of target chemical substance in the gas sampled.

12. The monitoring apparatus according to claim 6, wherein the sensor is an ion mobility sensor.

13. The gas sampling apparatus according to claim 1, wherein all of the sampling nozzles are disposed at different distances from the support surface.

14. A control method of a monitoring apparatus that investigates the state of an object,
   wherein the monitoring apparatus includes: a sampling unit that samples gas inside a separated space that is separated from the outside environment by an air curtain that covers the object; and a sensor that detects at least one chemical substance included in a gas sampled by the sampling unit, and the sampling unit includes a plurality of sampling nozzles disposed at different positions inside the separated space, and
   the control method comprises changing sampling conditions including at least one of a sampled amount, position, and movement of each of the plurality of sampling nozzles, and
   wherein the changing sampling conditions includes increasing a concentration of target chemical substance in the gas sampled.

15. The control method according to claim 14, wherein the changing sampling conditions includes changing sampling conditions of the plurality of sampling nozzles randomly or in accordance with a predetermined algorithm.

16. The control method according to claim 14, wherein the changing sampling conditions includes changing the sampling conditions of the plurality of sampling nozzles in accordance with a detection result of the sensor.

* * * * *